(12) United States Patent
Knoesen et al.

(10) Patent No.: US 10,400,270 B2
(45) Date of Patent: Sep. 3, 2019

(54) RNA-BASED, AMPLIFICATION-FREE, ORGANISM IDENTIFICATION USING NANO-ENABLED ELECTRONIC DETECTION

(71) Applicant: THE REGENTS OF THE UNIVERSITY OF CALIFORNIA, Oakland, CA (US)

(72) Inventors: Andre Knoesen, Davis, CA (US); Paul Alexander Feldstein, Sacramento, CA (US); Joshua Hihath, Woodland, CA (US); Erkin Seker, Davis, CA (US); Maria Louise Marco, Davis, CA (US); Bryce William Falk, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/701,752

(22) Filed: Sep. 12, 2017

(65) Prior Publication Data
US 2018/0066310 A1 Mar. 8, 2018

Related U.S. Application Data

(60) Division of application No. 14/675,958, filed on Apr. 1, 2015, now Pat. No. 9,803,234, which is a continuation of application No. PCT/US2013/063496, filed on Oct. 4, 2013.

(60) Provisional application No. 61/709,765, filed on Oct. 4, 2012.

(51) Int. Cl.
*C12Q 1/6825* (2018.01)

(52) U.S. Cl.
CPC ................ *C12Q 1/6825* (2013.01)

(58) Field of Classification Search
CPC ........ C12Q 1/6825; G01N 27/00; B01J 19/00
See application file for complete search history.

(56) References Cited

U.S. PATENT DOCUMENTS

| 6,582,954 | B2 | 6/2003 | Sato |
| 7,132,837 | B1 | 11/2006 | Tao |
| 7,435,384 | B2 | 10/2008 | Fish |
| 7,455,975 | B2 | 11/2008 | Henkens |

(Continued)

FOREIGN PATENT DOCUMENTS

EP 1620570 B1 9/2010

OTHER PUBLICATIONS

Epsilon Eclipse instruction Brochure, printed from BASI website on Nov. 2, 2018, pp. 1-92. (Year: 2018).*

(Continued)

*Primary Examiner* — Narayan K Bhat
(74) *Attorney, Agent, or Firm* — O'Banion & Ritchey LLP; John P. O'Banion

(57) ABSTRACT

A technique that uses nanotechnology to electrically detect and identify RNA sequences without the need for using enzymatic amplification methods or fluorescent labels. The technique may be scaled into large multiplexed arrays for high-throughput and rapid screening. The technique is further able to differentiate closely related variants of a given bacterial or viral species or strain. This technique addresses the need for a quick, efficient, and inexpensive bacterial and viral detection and identification system.

4 Claims, 7 Drawing Sheets
Specification includes a Sequence Listing.

(56) References Cited

U.S. PATENT DOCUMENTS 7,741,033 B2   6/2010 Kelley
2007/0072169 A1\* 3/2007 Peyvan .............. G01N 27/3277
                                                      435/4

OTHER PUBLICATIONS

Korean Intellectual Property Office (KIPO), International Search Report and Written Opinion dated Dec. 11, 2013, counterpart PCT International Application No. PCT/US2013/063496, pp. 1-12, with claims searched, pp. 13-16.
Venkatesan, Bala Murali et al., "Nanopore sensors for nucleic acid analysis", Nature Nanotechnology, vol. 6, No. 10, pp. 615-624 (2011).
Park, So-Jung et al., "Array-based electrical detection of DNA with nanoparticle probes", Science, vol. 295, No. 5559, pp. 1503-1506 (2005).
Tsai, C.-Y. et al., "Electrical detection of DNA hybridization with multilayer gold nanoparticles between nanogap electrodes", Microsystem Technologies, vol. 11, No. 2-3, pp. 91-96 (2005).

\* cited by examiner

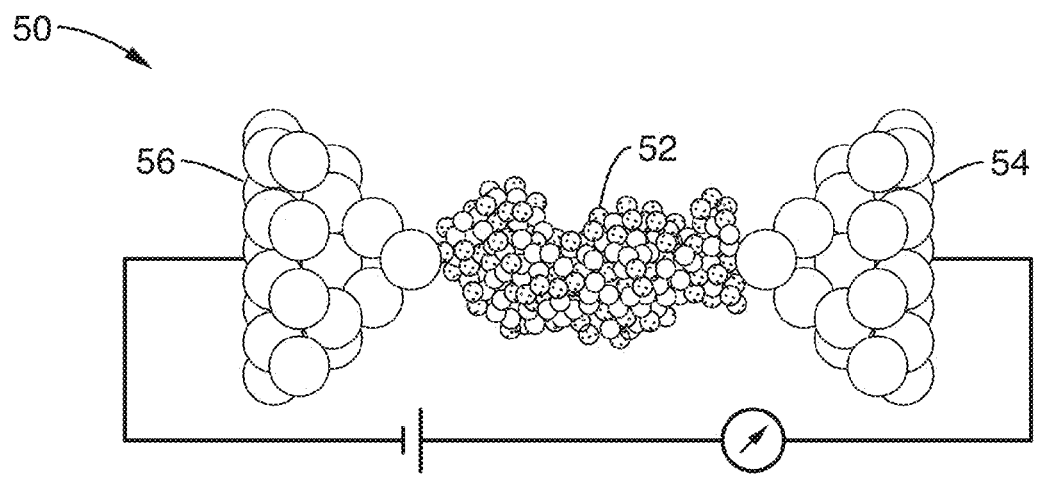
FIG. 2
DNA: NH$_2$-CCC - GCGCGCG - CCC-NH$_2$
SEQ. ID NO. 1:    N=13
FIG. 3
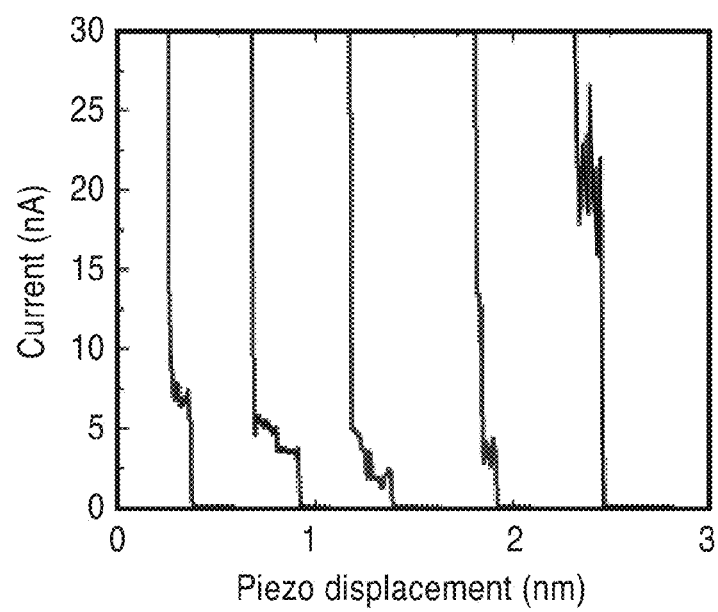
FIG. 4

RNA-BASED, AMPLIFICATION-FREE, ORGANISM IDENTIFICATION USING NANO-ENABLED ELECTRONIC DETECTION

CROSS-REFERENCE TO RELATED APPLICATIONS

This application is a division of U.S. patent application Ser. No. 14/675,958 filed on Apr. 1, 2015, incorporated herein by reference in its entirety, which is a 35 U.S.C. § 111(a) continuation of PCT international application number PCT/US2013/063496 filed on Oct. 4, 2013, incorporated herein by reference in its entirety, which claims priority to, and the benefit of, U.S. provisional patent application Ser. No. 61/709,765 filed on Oct. 4, 2012, incorporated herein by reference in its entirety. Priority is claimed to each of the foregoing applications.

The above-referenced PCT international application was published as PCT International Publication No. WO 2014/055888 on Apr. 10, 2014, which publication is incorporated herein by reference in its entirety.

INCORPORATION-BY-REFERENCE OF SEQUENCE LISTING

This application includes a sequence listing in a text file entitled "UC-2013-028-3-US-div-testsequence13-ST25.txt" created on Sep. 12, 2017 and having a 1 kb file size. The sequence listing is submitted through EFS-Web and is incorporated herein by reference in its entirety.

BACKGROUND OF THE INVENTION

1. Field of the Invention

This invention pertains generally to a system and methods for detecting and identifying RNA sequences in biological organisms, and more particularly to a technique that uses nanotechnology to electrically detect and identify RNA, including but not limited to bacterial and viral coding and non-coding RNA sequences, without the necessity of using enzymatic amplification methods or fluorescent markers.

2. Description of Related Art

Rapid, efficient, and low cost detection and identification of an organism based on its nucleic acid is a challenge facing those who care for plant and animal health. Current technologies, such as quantitative polymerase chain reaction (q-PCR), rely on multiple assays and amplification methods to identify organisms based on collected nucleic acid. Traditional optical detection methods also require fluorescent markers. These multiple independent steps and tests increase the processing time and cost of detection and identification. There is a clear and evident need to develop new technologies that can quickly, efficiently, and inexpensively identify organisms using their nucleic acid, especially microorganisms associated with plants and humans, based on genetic markers.

BRIEF SUMMARY OF THE INVENTION

Accordingly, the present invention provides a system and method that uses nanotechnology to electrically detect and identify an organism using RNA sequences without the need for enzymatic amplification methods or fluorescent markers. Although the present invention is described herein with reference to microorganisms, the present invention is applicable to detecting and identifying any biological organism based on the organism's genetic information.

The present invention addresses the need for a quick, efficient, and inexpensive microbial detection and identification system that may include, but is not limited to the detection and identification of bacteria and viruses. In cases where microbe densities are particularly low, the technique provides additional sensitivity that allows for the target molecules to be detected in small quantities. Furthermore, the technique may be scaled into large multiplexed arrays for high-throughput and rapid screening. The subject invention is further able to differentiate between closely related variants of a given bacterial or viral species or strain.

An aspect of the invention is a method of precise and highly sensitive detection and identification of bacteria and viruses in agricultural, medical, epidemiological, biosecurity, public health, and other applications.

Another aspect of the invention is to provide a platform that electrically detects genetic information (RNA) at the molecular level without the use of fluorescent markers.

Another aspect of the invention is to provide a platform that removes the need for enzymatic amplification (i.e., PCR).

Another aspect of the invention is to provide a platform for detection and identification of specific species and strains.

Another aspect of the invention is to provide a platform that is amenable to multiplexing and facile integration with electronics for field-deployable devices and high-throughput applications.

An embodiment of the present invention includes an electrical sensor platform to detect bacteria and viruses using nanotechnology to electrically detect RNA-based interactions for identification of microbes that cause plant and human diseases.

In another embodiment, the present invention includes an electrical sensor platform to detect food-borne bacteria and plant viruses.

In another embodiment, the system includes an integrated sensor platform that uses nanotechnology to electrically detect and identify coding and non-coding RNA sequences without the necessity of enzymatic amplification methods (PCR). In one embodiment, the method uses the natural amplification of RNA, and therefore, does not require the use of enzymatic amplification.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 2 is a schematic diagram of a single DNA:RNA hybrid bound between two electrodes.

FIG. 3 shows the example probe sequence (N=13) SEQ. ID. NO. 1 used in experiments.

FIG. 4 is a graph showing current vs. displacement traces for several single molecule junctions including the sample sequence from FIG. 3.

Figure 5:
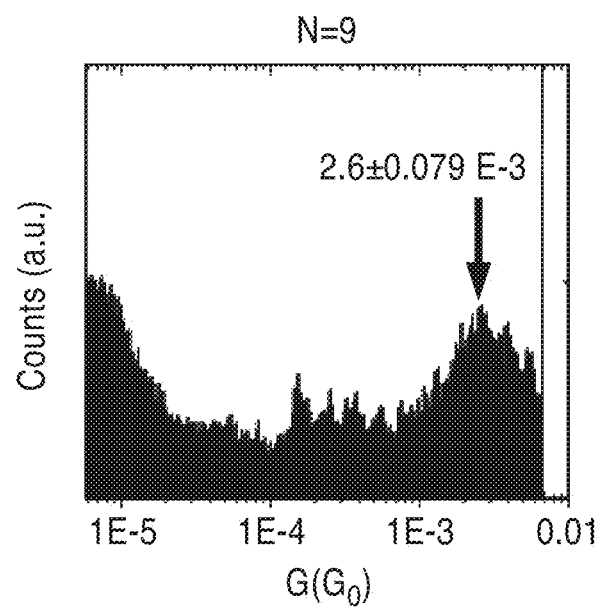

FIG. 5 is a histogram resulting from a statistical analysis of curves similar to that shown in FIG. 4 for the N=9 length hybrid system.

Figure 6:
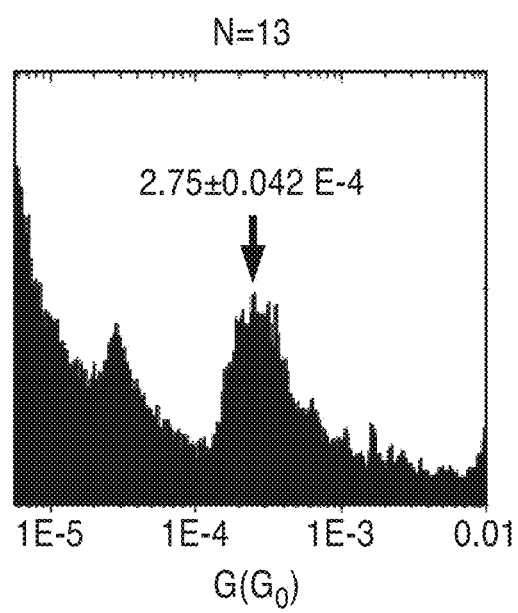

FIG. 6 is a histogram resulting from a statistical analysis of curves similar to that shown in FIG. 4 for the N=13 length hybrid system.

Figure 7:
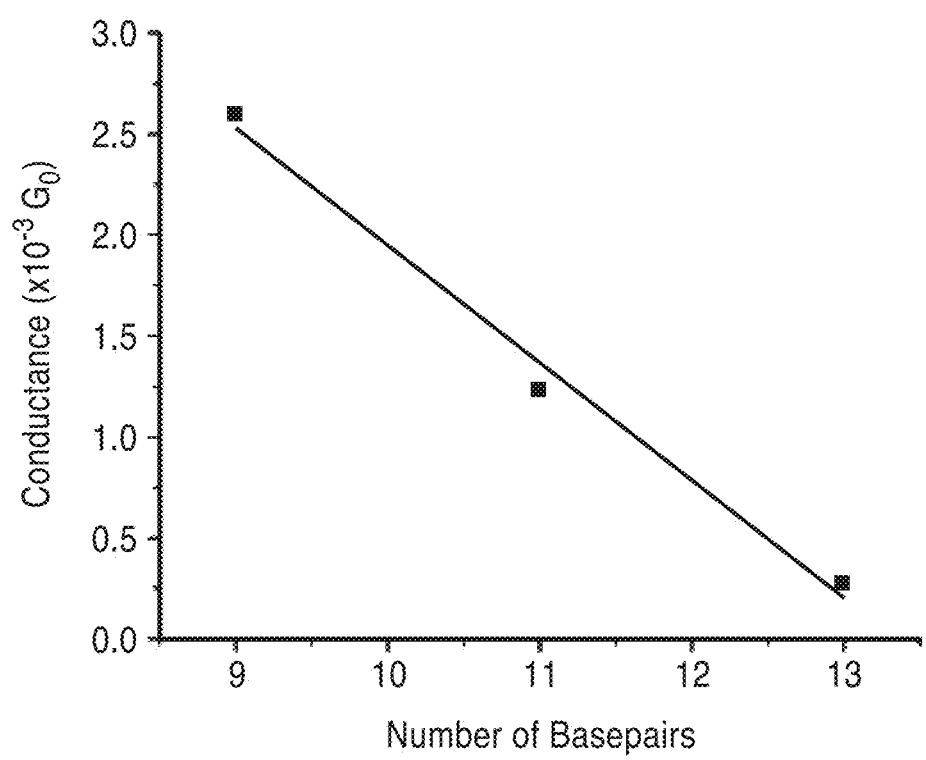

FIG. 7 is a graph of conductance vs. length for the sequences studied thus far.

FIG. 8A through FIG. 8D is a set of SEM images of nanoporous gold after different thermal treatments and the various morphologies caused by ligament coarsening.

Figure 9:
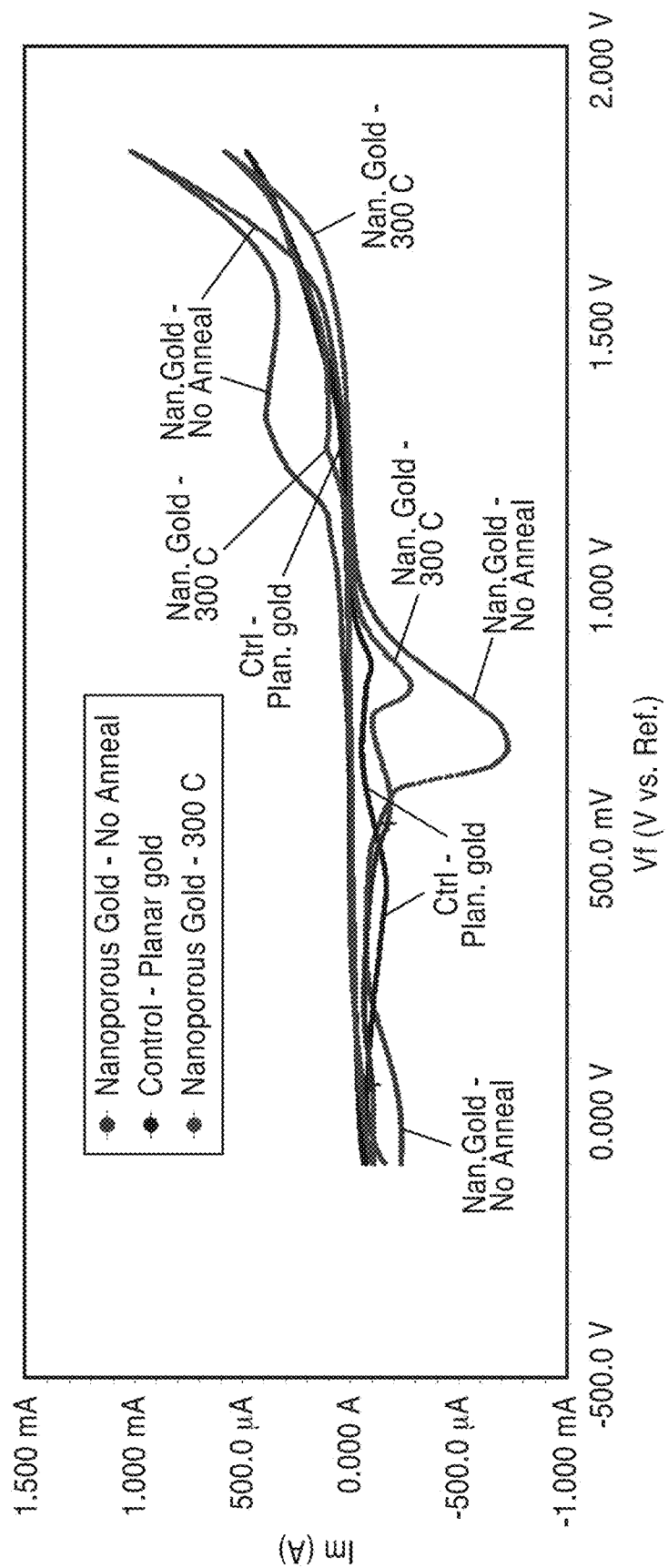

FIG. 9 is a graph showing the results of the surface area available for reaction when estimated electrochemically using dilute sulfuric acid as the electrolyte.

Figure 10:
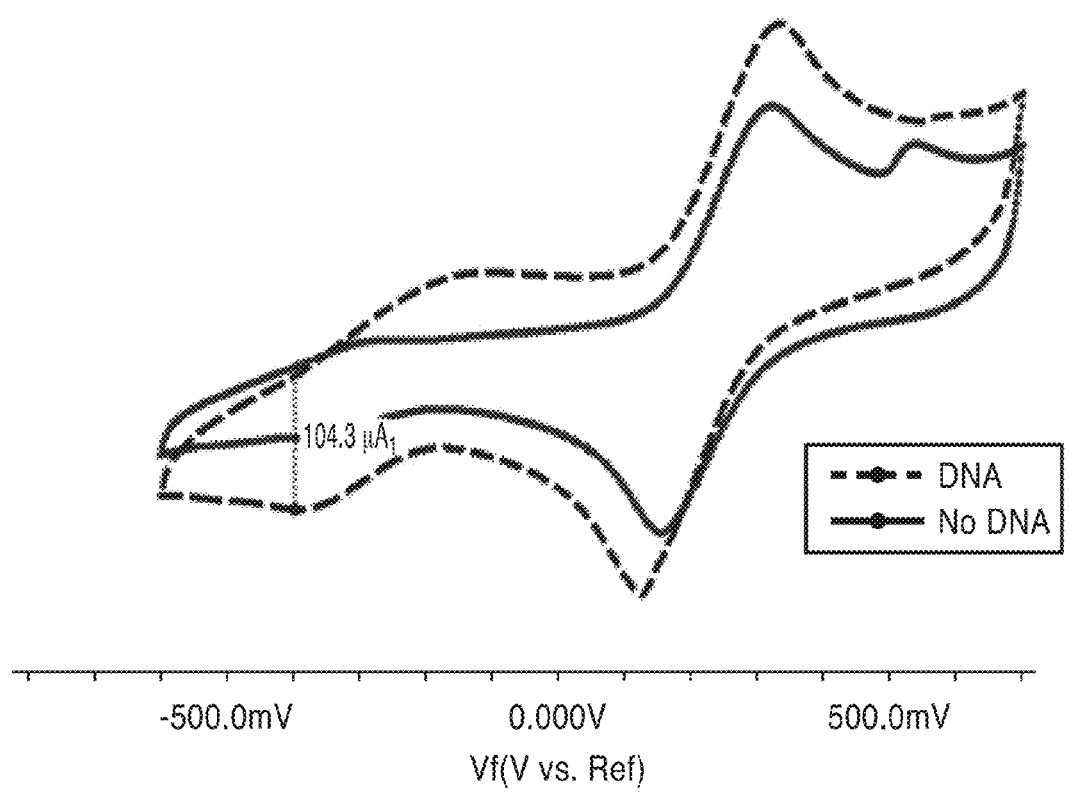

FIG. 10 is a graph showing the amount of DNA immobilized as estimated using ruthenium hexamine chloride and potassium ferrocyanide as redox markers.

DETAILED DESCRIPTION OF THE INVENTION

By way of example, and not of limitation, the present invention pertains to RNA-based, amplification-free, organism identification using nano-enabled electronic detection. The present invention further pertains to nano-molecular electronic detection of single molecule, RNA-based interactions for identification and characterization of organisms including microbes causing plant, animal, and human diseases. Accordingly, the present invention could be used to identify infectious diseases or to identify specific genes being transcribed in mammals and plants.

In another embodiment of the present invention, the presence of single nucleotide polymorphisms can be detected in a gene which can be used to detect genetic disorders and diseases.

In one embodiment, the method involves a two-tiered molecular based detection and identification approach where the first stage screens for specific microbe genus/species groups. Then, within the pathogen group, the second stage identifies specific microbe strains/pathotypes.

The initial prescreening stage uses electrochemical measurements enhanced by nano-scale mechanisms (e.g., increased surface area, nanoconfinement) to recognize hybridization events between the RNA targets and complementary thiolated DNA, PNA (peptide nucleic acid) or LNA (locked nucleic acid) probes bound to a nanostructured electrode surface. An active redox probe pair will then be used to electrochemically detect the hybridization between the target and probe serving to identify specific microbes/pathogens. The redox-based electrochemical detection of hybridization events that are detected by densely-packed probe molecules on nanoporous gold surfaces determines the microbe group. The nanoporous surface also acts as a nano-scale concentrator via charge-size specific confinement of target molecules of interest.

The samples are then analyzed by a final stage designed to provide highly selective identification of a specific strain within a microbe or pathogen group. In an alternative embodiment, this approach may be scaled into a large multiplexed array for high-throughput and rapid screening. This second stage involves using a nano-scale moveable electrode to make contact with the target molecules to obtain conductance information. The single nucleic-acid conductance measurements reveal target-probe strand match.

It will be appreciated that the subject invention does not require enzymatic amplification (e.g. PCR). Instead, it relies on RNA, including but not limited to mRNA and non-coding RNA (tRNA, rRNA, small RNAs), which microbes naturally amplify via transcription as they express their genetic information. Additionally, unique nano-scale enabled phenomena is utilized, including augmented effective surface area for high probe density and nano-cavity enabled pre-concentration of target species for additional sensitivity enhancement.

Unlike current optical detection methods, which do not directly detect genetic information (i.e. require the use of fluorescent markers), the present invention directly detects genetic information at the molecular level through electrical means.

Aspects of the present invention are founded on recent advances in nanotechnology and embodiments of the present invention are ultimately intended for hand-held devices which are field-ready for agriculture, food industries and healthcare.

Rapid, efficient, and low cost detection and identification of specific microbial pathogens including bacteria, viruses, and fungi is a challenge facing plant and animal (including human) health. The present invention addresses this challenge by providing a new technology to detect specific microorganisms within complex environmental media.

In one embodiment, the rapidly increasing number of genome sequences that are available for a wide range of microbes are used, including those which are pathogens of plants and/or animals. Even closely related variants of a given pathogen species, which may have important differences in host range and/or pathogenicity, differ in their genome sequences. In the subject invention, this information is exploited to detect specific pathogens.

While the majority of current nucleic acid detection approaches target DNA, the present invention uses "short" and "long" DNA oligomers to target RNA, as RNA offers many unexploited advantages over DNA. Transcription represents a natural amplification of RNA compared to its DNA template, thus more RNA is available. Second, controlled degradation of RNA into pieces small enough (even 15 to 20 nucleotides) to use with the two detection systems proposed here is more facile than it would be for DNA. Lastly, many plant and animal viruses have RNA genomes, and by targeting RNA, the need to convert RNA sequences into cDNA is obviated.

It is envisioned that the present unified multidisciplinary theme will make fundamental new contributions to the biological systems studied here, and to nano-molecular electronic engineering, and together lead to new technology for high-throughput, on-site, specific identification of plant-associated microbes causing plant and human diseases.

The invention may be better understood with reference to the accompanying examples, which are intended for purposes of illustration only and should not be construed as in any sense limiting the scope of the present invention as defined in the claims appended hereto.

Example 1

Figure 1:
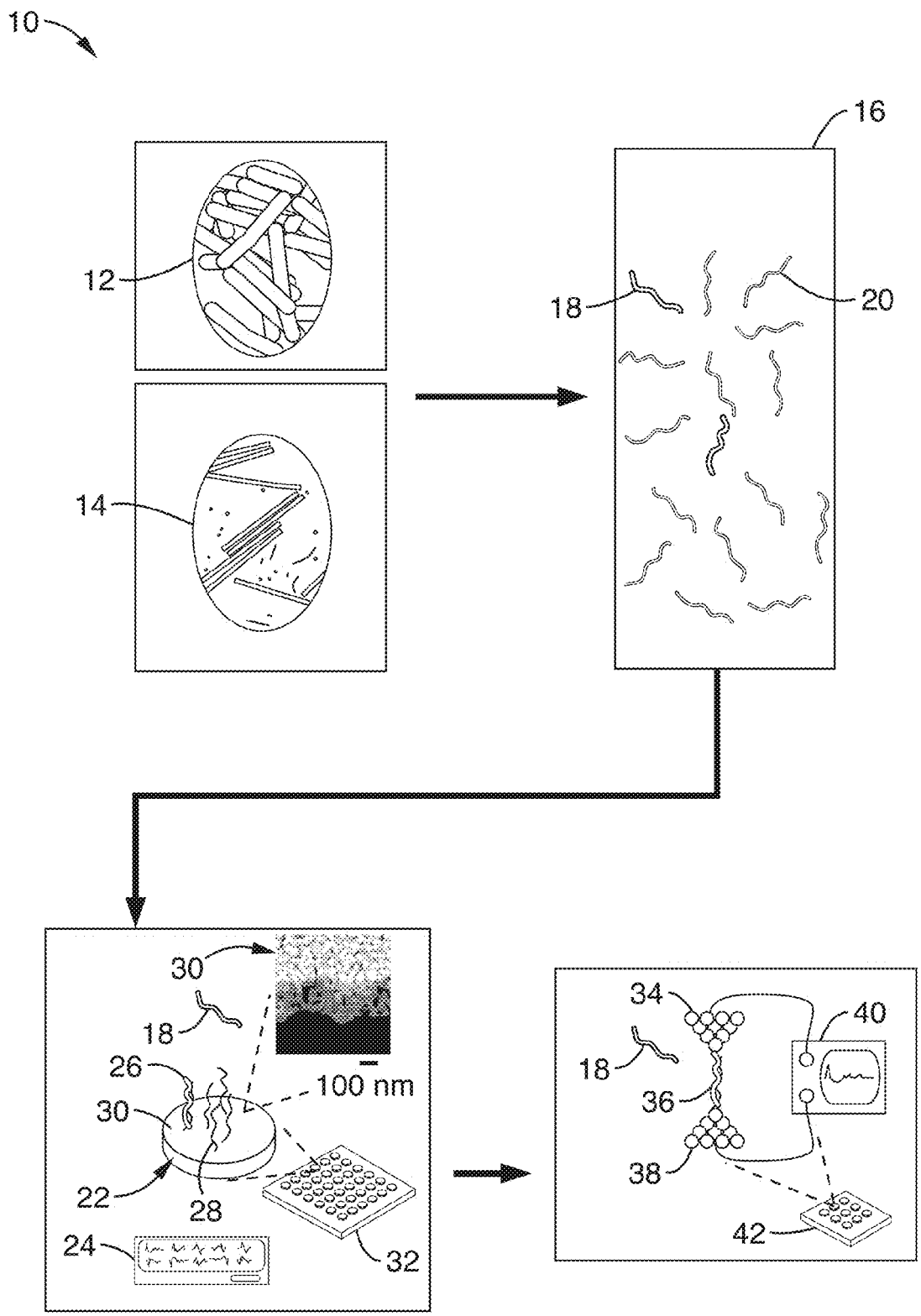
FIG. 1 is a schematic diagram of an electrical sensor platform to detect bacteria and viruses according to one embodiment of the invention.

FIG. 1 shows a schematic diagram of an electrical sensor platform 10 to detect bacteria 12 (i.e. food-borne bacteria) and viruses 14 (i.e. plant viruses) according to an embodiment of the subject invention. After fragmentation 16 of the RNA into target 18 and non-target 20 nucleic acid fragments, the fragments are transported to a stage 22 that rapidly screens for organism/microbe/pathogen groups using redox-based electrochemical detection of hybridization events 26. These hybridization events 26 are detected using densely-packed probe molecules (sequences) 28 bound to nanoporous gold electrode surfaces 30 and a device for measuring electrical current 24, such as a potentiostat. A magnified image of the stage 22 surface with the gold electrode surfaces 30 is shown.

This electrochemical approach can be scaled into large multiplexed arrays 32 for high-throughput and rapid screening. Thiolated "probe" sequences 28 that are complementary to the RNA target 18 sequences are bound to a nanoporous electrode surface 30. Hybridization events 26 between the target 18 and probe sequences 28 are detected using an electrochemically active redox probe pairs, such as $Ru(NH_3)_6^{3+}/Fe(CN)_6^{3-}$. The non-target nucleic acid fragments 20 that do not bind to the probe sequences 28 settle out.

The samples are next analyzed by a final stage designed to provide, for example, highly-selective identification of specific strains within a microbe or pathogen group. It is based on single nucleic-acid conductance measurements that reveal target-probe strand match. The electrical read-out capability of such technology enables facile integration with sensor electronics, and is thus amenable to facile integration with instrumentation electronics and field-deployable devices, responding to applications where "sample-to-answer" time is critical.

The final stage is based on a molecular conductance detection to provide greater specificity. Here, a nanoscale moveable electrode 34 is used to make repeated contact with a hybridized target-probe pair 36 bound to a second electrode 38 to obtain conductance information 40. The electrical resistance of short DNA duplexes is extremely sensitive to sequence, length, and even single nucleotide polymorphisms. In this embodiment, the focus is on detecting microbial RNA and identifying specific microbial strains. However, this method can be used to detect mutations in genes that result in specific characteristics or diseases.

This final stage will only need to be implemented in "small" multiplexed arrays 42. Furthermore, in cases where microbe densities are particularly low (<10 cfu/plant), the single-molecule conductance approach will provide additional sensitivity since extremely small quantities of target molecules 18 will still provide a useable signal.

The prescreening stage is focused on speed and efficiency using a large multiplexed array format to select for specific organisms based on their genomic information. It serves to identify specific organisms, but does not resolve small mismatches between target and probe nucleic acid sequences. The final detection stage is optimized for selectivity and sensitivity to uniquely identify specific genetic markers characteristic of individual target organisms.

This effort provides an exciting new paradigm for detecting specific RNA targets from an extremely small number of sample molecules and has wide ranging potential applications.

Example 2

In order to determine whether unique genetic sequences could be detected with the approach described, an in silico preliminary study was undertaken using the nucleic acid sequences of strains 4, 5, and 6 of grapevine leafroll-associated viruses, which are 13830, 13384 and 13807 nucleotides in length respectively. In silico ribonuclease A-digestion of these sequences, followed by sorting of the residual sequences by length and comparison between strains was carried out. This analysis identified 3, 4 and 9 unique residual fragments of lengths ranging from 15 to 20 nucleotides from strains 4, 5 and 6 respectively. These 16 sequences had an average GC content of 48.5 percent, which shows that hybridization is reasonable.

Example 3

Experimental evidence has been obtained to demonstrate the feasibility of using single-molecule conductance measurements to detect specific RNA sequences and identify a specific strain of microorganism.

Direct measurement of the electrical conductance of hybrid DNA:RNA molecules was demonstrated in a liquid environment at the single-molecule level by using nanoscale electrodes to directly interrogate the electrical properties of the hybrid molecular junction. Notable differences in the conductance properties of DNA:RNA hybrid sequences were observed, and it has been experimentally shown that the conductance of such hybrid systems is sensitive to the number of base pairs in the stack, which offers the required specificity to the sensor.

Three DNA probe sequences with lengths of 9, 11, and 13 base pairs were synthesized with amine terminal groups on both the 5' and 3' ends. These terminal groups allow direct linkage to atomically sharp gold electrodes. In an aqueous environment consisting of 100 mM phosphate buffer solution at pH 7.4, the DNA probe sequence and the complementary RNA target sequence were hybridized by heating the solution to 80° C. and cooling to room temperature over the course of three hours.

Once the DNA and RNA sequences are hybridized, the conductance measurements were performed on three GC-only sequences with lengths of 9, 11, and 13 base pairs, as shown in FIG. 2 through FIG. 7. FIG. 2 through FIG. 7 show the different aspects of conductance measurements of DNA:RNA hybrid molecules. FIG. 2 is a schematic illustration 50 of a single DNA:RNA hybrid 52 bound between two electrodes 54, 56. The conductance of each hybrid duplex 52 is measured by repeatedly bringing the nanoscale gold electrodes 54, 56 into contact and withdrawing them in the presence of the buffer solution containing the DNA:RNA hybrids 52. Conductance was measured using a transimpedance amplifier.

FIG. 3 shows an example of the N=13 sequence, SEQ. ID. NO. 1, that was used in the experiments. The DNA probe is terminated with amines so that it will bind to the gold electrodes. The target RNA sequence was complementary to the probe SEQ. ID. NO. 1 sequence of FIG. 3.

If molecules bind between the electrodes 54, 56 during the withdrawal process, steps appear in the current vs. displacement trace as shown in FIG. 4. FIG. 4 shows a graph of the current versus displacement resulting from electrode withdrawal. Steps indicate the binding of molecules between the two electrodes. By repeating these measurements thousands of times for each sequence, a statistically significant amount of information is gathered, and a statistical analysis yields the most likely conductance of a single molecule. A histogram is constructed from thousands of current vs. time (or electrode separation) traces for statistical analysis and yields the most likely conductance of a single oligonucleotide duplex.

The results for two DNA:RNA hybrids are shown in FIG. 5 and FIG. 6. FIG. 5 and FIG. 6 show histograms resulting from a statistical analysis of curves similar to that shown in FIG. 4 for the N=9 and N=13 length hybrid systems, respectively. There are distinct differences between the statistical distribution of the conductance associated with each duplex, which demonstrates that break-junction conductance measurements have the capability of detecting specific RNA sequences.

FIG. 7 shows a graph illustrating conductance vs. length for the sequences that have been studied thus far, demonstrating that the conductance of DNA:RNA hybrids can be measured, and that the conductance is sensitive to molecular length.

Example 4

The following results demonstrate that the nano-scale features of nanoporous (np) gold produces a higher electrochemically active area compared to a planar gold electrode. This enhances the electrical current that is generated in the presence of a nucleic acid, which in turn augments detection sensitivity.

Figure 8A:
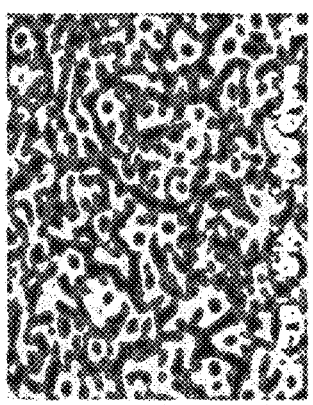
Figure 8B:
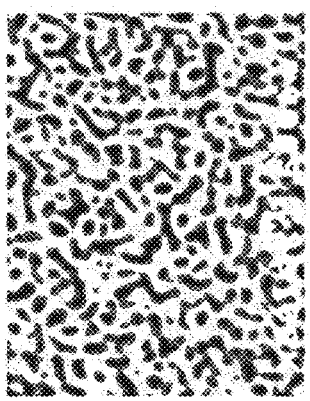
Figure 8C:
Figure 8D:
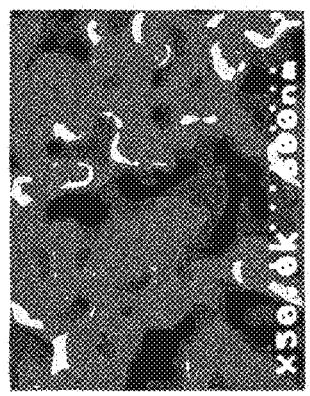

Nanoporous gold (np-Au) samples were synthesized by depositing a thin film alloy (~70% gold and 30% silver by atomic weight) and subsequently etching the alloy with nitric acid. This process removed silver and produces nanoporosity through the re-organization of gold atoms into ligaments. Thermal treatment of np-Au produces various morphologies, as shown in the SEM images of FIG. 8A through FIG. 8D, via ligament coarsening. FIG. 8A shows the np-Au with no annealing at room temperature. FIG. 8B, FIG. 8C and FIG. 8D show the annealing morphologies at 200° C., 300° C. and 400° C., respectfully.

The surface area available for reaction is estimated electrochemically using dilute sulfuric acid as the electrolyte. Np—Au films that are not thermally treated yield seven times higher surface area compared to that of a planar gold surface as shown in FIG. 9.

In order to investigate the effect of DNA probe adsorption onto the surface, thiolated ss-DNA probes were immobilized onto the np-Au working electrode. Ruthenium hexamine chloride and potassium ferrocyanide were used as the redox markers. In this detection scheme, ruthenium cations were attracted to the negatively-charged DNA backbone and underwent reduction. The amount of DNA immobilized can be estimated using this redox marker as shown in FIG. 10. Ferrocyanide regenerates the reduced ruthenium cations.

All cited references are incorporated herein by reference in their entirety. In addition to any other claims, the applicant(s)/inventor(s) claim each and every embodiment of the invention described herein, as well as any aspect, component, or element of any embodiment described herein, and any combination of aspects, components or elements of any embodiment described herein.

From the discussion above it will be appreciated that the invention can be embodied in various ways, including the following:

1. A method for identifying organisms, the method comprising: providing a target RNA molecule from an organism; contacting, under hybridizing conditions, the target RNA molecule with a complementary nucleic acid probe, said probe attached to a nanostructured electrode, wherein hybridization of the target RNA molecule and complementary nucleic acid probe provides an electrochemical current; measuring said electrochemical current; and identifying the organism based on said electrochemical current measurement.

2. The method of any preceding embodiment, further comprising: providing a hybridized target RNA molecule and complementary nucleic acid probe pair; binding the hybridized target RNA molecule and complementary nucleic acid probe pair to a first nanoscale electrode; repeatedly contacting the hybridized target RNA molecule and complementary nucleic acid probe pair with a second nanoscale electrode; measuring conductance, wherein nucleic acid matches and mismatches between the target RNA molecule and complementary nucleic acid probe are detected based on said conductance; and further characterizing the organism based on said nucleic acid matches and mismatches.

3. The method of any preceding embodiment, wherein the organism is a microbe.

4. The method of any preceding embodiment, wherein the complementary nucleic acid probe is a molecule selected from the group consisting of a deoxyribonucleic acid (DNA), a peptide nucleic acid (PNA) and a locked nucleic acid (LNA).

5. The method of any preceding embodiment, wherein the method is performed on a large scale multiplex array to allow for a rapid detection of a plurality of organisms.

6. The method of any preceding embodiment, wherein hybridization between the target RNA molecule and complementary nucleic acid probe is detected using an electrochemically active redox probe pair.

7. The method of any preceding embodiment, wherein the electrochemically active redox probe pair comprises $Ru(NH_3)_6^{3+}/Fe(CN)_6^{3-}$.

8. The method of any preceding embodiment: wherein the nanoscale electrodes comprise a noble metal; and wherein the complementary nucleic acid probe contains a chemical linker terminal group on both 5' and 3' ends that attaches to the nanoscale electrodes.

9. The method of any preceding embodiment, wherein the nanostructured electrode surface is nanoporous and has a large surface area allowing for a higher complementary nucleic acid probe density than a planar surface and a higher electrochemically active platform for higher target RNA molecule detection sensitivity.

10. The method of any preceding embodiment, wherein natural amplification of the target RNA molecule is used.

11. The method of any preceding embodiment, wherein the conductance is used to determine a mutation in a gene, said mutation resulting in a disease.

12. A method for identifying the strain of an organism, the method comprising: providing a target RNA molecule from an organism; contacting, under hybridizing conditions, the target RNA molecule with a complementary nucleic acid probe; binding the hybridized target RNA molecule and complementary nucleic acid probe to a first nanoscale electrode; repeatedly contacting the hybridized target RNA fragment and complementary nucleic acid probe with a second nanoscale electrode; measuring conductance, wherein nucleic acid matches and mismatches between the target RNA molecule and complementary nucleic acid probe are detected based said conductance; and further characterizing the organism based on said nucleic acid matches and mismatches.

13. The method of any preceding embodiment, wherein the organism is a microbe.

14. The method of any preceding embodiment, wherein the complementary nucleic acid probe is a molecule selected from the group consisting of a deoxyribonucleic acid (DNA), a peptide nucleic acid (PNA) and a locked nucleic acid (LNA).

15. The method of any preceding embodiment: wherein the nanoscale electrodes comprise a noble metal; and wherein the complementary nucleic acid probe contains a chemical linker terminal group on both 5' and 3' ends that attaches to the nanoscale electrodes.

16. An apparatus for detecting and identifying target RNA sequences, the apparatus comprising: a first stage, wherein said first stage comprises nanostructured noble metal electrodes; nucleic acid probe molecules, wherein said nucleic acid probe molecules are complementary to a target RNA molecule and wherein said nucleic acid probe molecules are bound to said nanostructured noble metal electrodes; a connector for connecting said first stage to a potentiostat, wherein hybridization between the target RNA molecule and complementary nucleic acid probe is detected by said potentiostat using an electrochemically active redox probe pair.

17. The apparatus of any preceding embodiment, further comprising: a second stage comprising nanoscale electrodes, wherein a hybridized target RNA molecule and complementary nucleic acid probe pair is bound to a first nanoscale electrode and then repeatedly contacted with a second nanoscale electrode; and a connector for connecting said second stage to a transimpedance amplifier, said transimpedance amplifier configured for receiving a conductance of the target RNA molecule and complementary nucleic acid probe.

18. The apparatus of any preceding embodiment, wherein natural amplification of the target RNA molecule is used.

19. The apparatus of any preceding embodiment, wherein the conductance is used to determine a mutation in a gene, said mutation resulting in a disease.

20. The apparatus of any preceding embodiment: wherein the nanoscale electrodes comprise a noble metal; and wherein the complementary nucleic acid probe contains a chemical linker terminal group on both 5' and 3' ends that attaches to the nanoscale electrodes.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

---

---

What is claimed is:

1. An apparatus for detecting and identifying target RNA sequences, the apparatus comprising:
   a first stage, wherein said first stage comprises one or more nanostructured noble metal electrodes;
   nucleic acid probe molecules, wherein said nucleic acid probe molecules are complementary to a target RNA molecule and wherein said nucleic acid probe molecules are bound to said nanostructured noble metal electrodes of the first stage;
   a first connector for connecting said first stage to a potentiostat, wherein hybridization between the target RNA molecule and complementary nucleic acid probe is detected by said potentiostat using an electrochemically active redox probe pair;
   a second stage comprising one or more nanoscale electrodes; and
   a second connector for connecting said second stage to a transimpedance amplifier, said transimpedance amplifier configured for receiving a conductance of the target RNA molecule and complementary nucleic acid probe;
   wherein a hybridized target RNA molecule and complementary nucleic acid probe pair bound to said first nanoscale electrode are repeatedly contacted with at least one second stage nanoscale electrode.

2. The apparatus of claim 1, wherein natural amplification of the target RNA molecule is used.

3. The apparatus of claim 1, wherein the conductance is used to determine a mutation in a gene, said mutation resulting in a disease.

4. The apparatus of claim 1:
wherein the nanoscale electrodes comprise a noble metal; and
wherein the complementary nucleic acid probe contains a chemical linker terminal group on both 5' and 3' ends that attaches to the nanoscale electrodes.

* * * * *

SEQUENCE LISTING

<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: Man made test sequence

<400> SEQUENCE: 1
cccgcgcgcg ccc      13